United States Patent
Kolder et al.

(10) Patent No.: US 6,735,473 B2
(45) Date of Patent: *May 11, 2004

(54) DEFIBRILLATOR ENCLOSURE WITH ALARM SIGNAL

(75) Inventors: Robert D. Kolder, 661 Morningside Ct., Schaumburg, IL (US) 60173; Timothy Strok, 9333 Beaver Pond Ct., Crystal Lake, IL (US) 60014; William R. Sears, Tinley Park, IL (US); Kevin J. Cronin, Elk Grove Village, IL (US)

(73) Assignees: Robert D. Kolder, Schaumburg, IL (US); Timothy Strok, Crystal Lake, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,461

(22) Filed: Oct. 5, 2001

(65) Prior Publication Data

US 2003/0032987 A1 Feb. 13, 2003

Related U.S. Application Data

(63) Continuation of application No. 09/355,149, filed on Jun. 17, 1999, now Pat. No. 6,301,501.

(51) Int. Cl.[7] ............................................... A61N 1/39
(52) U.S. Cl. .......................................................... 607/5
(58) Field of Search ..................... 607/1, 5; 340/286.07, 340/288, 289, 296, 301, 825.31, 825.32, 541–543, 545, 568, 571, 573; 200/61.62, 61.63

(56) References Cited

U.S. PATENT DOCUMENTS

| 3,644,920 | A | | 2/1972 | Cartledge |
| 4,015,250 | A | | 3/1977 | Fudge |
| 4,052,718 | A | | 10/1977 | Tucci |
| 4,663,621 | A | | 5/1987 | Field |
| 5,388,570 | A | | 2/1995 | Wassil |
| 5,568,123 | A | | 10/1996 | Derheim |
| 6,293,962 | B1 | * | 9/2001 | Bishay .......................... 607/1 |

* cited by examiner

*Primary Examiner*—Jeffrey R. Jastrzab
(74) *Attorney, Agent, or Firm*—Meroni & Meroni, P.C.; P. Derek Pressley; Charles F. Meroni, Jr.

(57) ABSTRACT

The defibrillator storage device has an enclosure comprised of wall sections, a top section, bottom section and door section defining an interior compartment of sufficient size to house a defibrillator. A defibrillator mount is connected to the interior of the enclosure. An alarm means having a visual alarm signal and an audible alarm signal is used to indicate that the door of the device has been opened, signaling a possible cardiac arrest incident. An activation switch for triggering the alarm is connected to the door and positioned to contact an enclosure wall when the door is closed. The normally open switch is closed and is closed when the door is opened. An alarm deactivating switch connected in circuit to the alarm is used to reset the system or to totally deactivate the alarm.

21 Claims, 8 Drawing Sheets

DEFIBRILLATOR ENCLOSURE WITH ALARM SIGNAL

PRIOR HISTORY

This is a Continuation in Part Patent Application of Non-Provisional Patent Application Ser. No. 09/335,149 filed Jun. 17, 1999 now U.S. Pat. No. 6,301,501.

BACKGROUND OF THE INVENTION

1. Field of the Invention

The present invention relates to a protective defibrillator storage device with an alarm system to notify others that a cardiac arrest incident is in progress.

2. Description of the Prior Art

Defibrillators are used by clinicians to resuscitate patients during a cardiac arrest. The availability of a defibrillator and a trained clinician to utilize the defibrillator during a cardiac arrest are often critical to the survival of a cardiac arrest victim. As the level of defibrillator technology grew, defibrillators were developed which required minimal training to apply and operate during cardiac arrest. These defibrillators, typically called Automated External Defibrillators (AED), have sophisticated cardiac assessment programs which allowed the AED to assess the status of the cardiac arrest victim and automatically defibrillate the cardiac arrest victim when it is appropriate.

Since it is often beneficial to defibrillate a cardiac arrest victim at the onset of cardiac arrest, the AED is being used more and more by non-clinicians in settings where it is often difficult or impossible for fully trained medical personnel to respond quickly to a cardiac arrest. Consequently, AEDs are being utilized in planes, office buildings, and other locations where medical personnel are not readily available. As a result of this growing use of AEDs and the need to protect the AED from unnecessary wear and tear and theft, a need has arisen for an adequate storage facility to protect the AED and to minimize the searching necessary to locate the AED during a cardiac arrest situation.

In a typical hospital setting, defibrillators are often placed on mobile carts called "crash carts". These carts typically have several drawers in which are placed various medicaments and supplies which are used by clinicians during cardiac arrests. Several of these "crash carts" are often located throughout the hospital. However, crash carts are typically not feasible in many applications outside of the clinical setting. One of the biggest drawbacks to these crash carts is the size of the cart. In a non clinical setting, users of the AED are typically not sufficiently trained to deliver medicaments and the storage space allotted for an AED is minimal, so a bulky crash cart is typically not required.

Also, during a cardiac arrest, it is often necessary to have several people present in order to assist with the resuscitation of the cardiac arrest victim. In most major hospitals, sophisticated warning systems are in place to notify appropriate personnel that a cardiac arrest is currently taking place. In locations where an AED may be used, there is often no system in place to notify others that a cardiac arrest is occurring. Consequently, it would be beneficial that the use of an AED start a signal process which would alert others of an occurrence of a cardiac arrest.

U.S. Pat. No. 4,015,250 issued to Fudge ("the '250 Patent") discloses an enclosure for housing a fire extinguisher with an electrically energizable warning device connected to the enclosure that has a resilient member to grip the body of the fire extinguisher. The resilient member merely holds the fire extinguisher in place with the fire extinguisher resting on the floor of the enclosure and does not promote awareness of the fire extinguisher. However, the '250 Patent does not disclose an enclosure having a mount that allows greater viewability of the contents of the enclosure. The claimed invention provides a defibrillator mount that retains the defibrillator within the enclosure in a location that provides improved viewability of the contents of the enclosure, thus promoting greater awareness of what type of equipment is inside the enclosure. Although differing sizes of defibrillators are contemplated to be used with the claimed invention, smaller defibrillators would not be easily viewed if held by the resilient member disclosed by the '250 Patent. The '250 Patent also does not disclose the use of a defibrillator housed in an enclosure for use in non-clinical settings such as office buildings and shopping malls. Using a defibrillator in combination with an enclosure of this type allows greater access to the use of a defibrillator, drastically cutting the response time associated with the deployment of the defibrillator to the victim or the victim to the defibrillator.

U.S. Pat. No. 5,388,570 issued to Wassil ("the '570 Patent") discloses a cabinet housing CPR masks and non-sterile hypoallergenic gloves having a lever switch on the cabinet automatically activating a loud piezo buzzer mounted on top of the cabinet when the cabinet door is opened that can be deenergized with a key-activated switch. However, the '570 Patent does not disclose an enclosure having a transparent door section and a mount that allows greater viewability of the contents of the enclosure through the transparent section of the door. Further, the '570 Patent does not disclose the use of a defibrillator being housed in an enclosure for use in non-clinical settings.

U.S. Pat. No. 3,644,920 issued to Cartledge ("the '920 Patent") discloses a panel mounting a hook having an upturned end and is adapted to support an article and an actuator bar pivoted to the panel overlying the hook so that if an article is removed from the hook the bar is displaced. An alarm circuit is actuated by displacement of the bar and includes a normally open switch adapted to be closed by the bar when displaced. This prior art is relevant in that it discloses the use of a relay circuit. However, the '920 Patent does not does not disclose an enclosure having a transparent door section and a mount that allows greater viewability of the contents of the enclosure through the transparent section of the door. Further, the '920 Patent does not disclose the use of a defibrillator being housed in an enclosure for use in non-clinical settings.

Accordingly, there is a need for a storage device which is easily locatable and can protect a defibrillator, particularly an AED, from unnecessary wear and tear and theft.

Accordingly there is also a need for a storage device for a defibrillator which can alert others that a cardiac arrest situation is occurring.

The present invention is a protective defibrillator storage device with an alarm system to notify others that a cardiac arrest incident in progress.

As will be described in greater detail hereinafter, the present invention solves the aforementioned and employs a number of novel features that render it highly advantageous over the prior art.

SUMMARY OF THE INVENTION

Accordingly it is an object of this invention to provide a storage device for a defibrillator that is easily locatable and capable of protecting the defibrillator from unnecessary wear and tear and theft.

A further object of the present invention is to provide a storage device for a defibrillator that is capable of alerting others that a cardiac arrest incident is in progress.

A further object of the present invention is to provide a storage device for a defibrillator in combination with a defibrillator.

To achieve these objectives, and in accordance with the purposes of the present invention the following protective defibrillator storage device with an integral alarm system is provided. Using the defibrillator storage device in combination with a defibrillator is also provided.

The protective defibrillator storage device has an enclosure comprised of a plurality of wall sections, a top section, a bottom section and a door section. The wall sections, top section, bottom section, and the door section define an interior compartment. The interior compartment is of sufficient size to house a defibrillator. A locking mechanism is typically connected to the door section and a wall section in order to secure the door in a closed position. The enclosure is typically mounted onto the surface of a wall but a stabilizing base may be attached in order to allow the enclosure to stand on its own. Retaining flanges can also be connected to an exterior surface of the enclosure to allow the enclosure to be easily recessed into a wall.

The enclosure is preferably made of 14 GA CRS steel with a high gloss finish, but other rigid lightweight materials can also be used. A portion of the door section is preferably made of a translucent material in order to allow visibility of the interior compartment when the door section is closed.

A defibrillator mount is connected to an interior surface of the enclosure. The defibrillator mount should hold the defibrillator so as to provide greater visibility of the defibrillator within the interior compartment. However, the defibrillator mount should also allow for quick removal of the defibrillator from the enclosure. Different embodiments of the defibrillator mount are contemplated with a first embodiment consisting of first and second retaining members, the first retaining member angularly extending from the interior surface toward the second retaining member, the second retaining member vertically adjacent the first retaining member extending substantially perpendicular from the interior surface having a retaining lip angularly extending from the second retaining member toward the first retaining member. A second embodiment of the defibrillator mount consists of at least one holding member extending generally perpendicularly from an interior surface of the enclosure, the holding member holding the defibrillator within the enclosure so that it can be readily viewed through the transparent portion of the door in embodiments of the invention having doors with transparent door sections.

An alarm means is connected to the enclosure. The alarm means is used to indicate that the door of the protective defibrillator storage device has been opened, and that a cardiac arrest incident is possibly in progress. The alarm means is comprised of an alarm circuit with a visual alarm signal and an audible alarm signal. The alarm means is activated when the door section is opened and remains activated until the alarm means is deactivated and reset.

An activation switch for triggering the alarm means is connected to the door section and operatively positioned to contact an enclosure wall when the door is closed. The activation switch is open when the door section is closed, but upon opening of the door section, the activation switch closes activating the alarm means.

An alarm deactivating switch is connected to the enclosure and is connected in circuit to the alarm means. The alarm deactivating switch is used to reset the system after the alarm means has been activated or to totally deactivate the alarm means. The alarm deactivating switch is a key switch connected in circuit to a power supply and to the alarm means. When the alarm means has been activated, the key switch is turned to an open position cutting of power to the alarm means and disabling the alarm. The defibrillator can then be reinserted into the protective defibrillator storage device and the door closed. The key switch is then rotated to the closed position, and the circuit between the power supply and the alarm circuit is completed and the alarm circuit is enabled.

The protective defibrillator storage device is typically positioned in a highly visible and relatively accessible area. The rugged construction of the protective defibrillator storage device protects the defibrillator from inadvertent impact and provides an easily locatable housing for the defibrillator. In case of a cardiac arrest, the protective defibrillator storage device is opened and the defibrillator is removed triggering the alarm means. The audible alarm signal and the visual alarm signal alert others that a potential cardiac arrest incident may be in progress and that assistance may be needed. Since the opening of the door section will trigger a visual alarm signal and an audible alarm signal, the protective defibrillator storage device will also alert others that the defibrillator has either been stolen or tampered with.

Other objects, features, and advantages of the invention will become more readily apparent upon reference to the following description when taken in conjunction with the accompanying drawings.

DESCRIPTION OF THE PREFERRED EMBODIMENT

The present invention is a protective defibrillator storage device with an integral alarm system to warn others that a cardiac arrest situation may be in progress.

Figure 1:
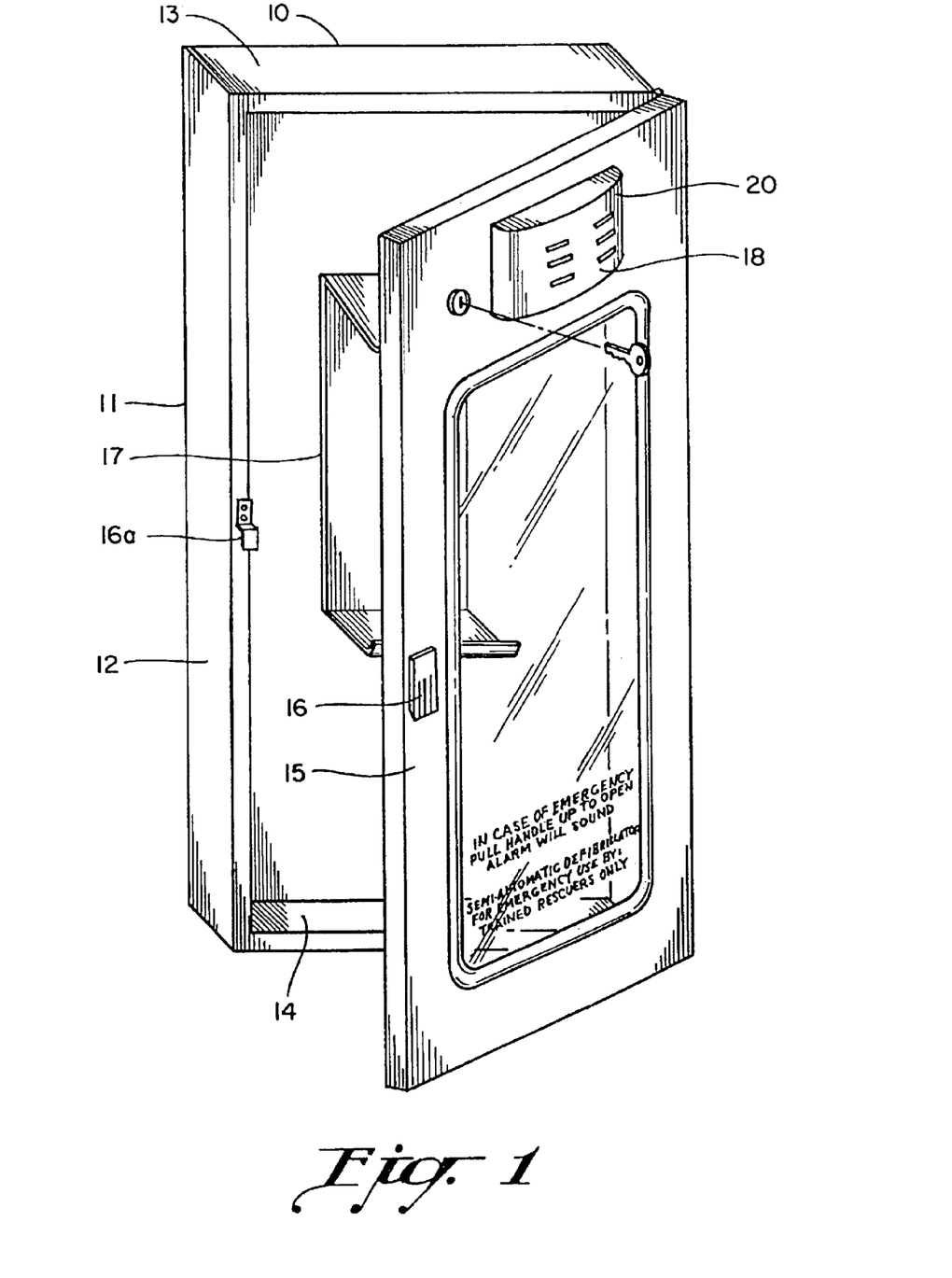
FIG. 1. A front view of the protective defibrillator storage device with the door section partially open.
Figure 2:
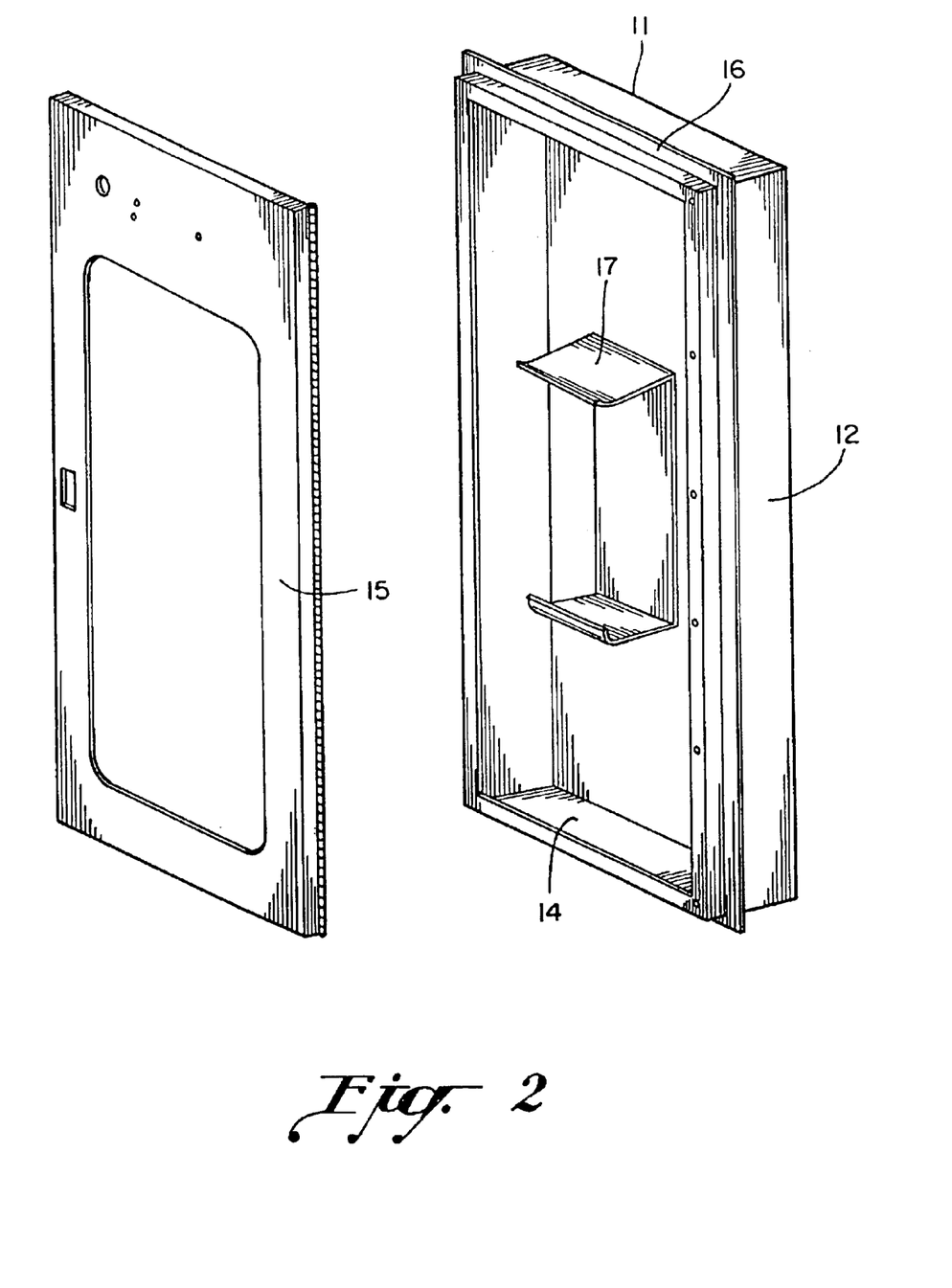
FIG. 2. An exploded view of the enclosure section revealing the interior of the enclosure section.
Figure 3:
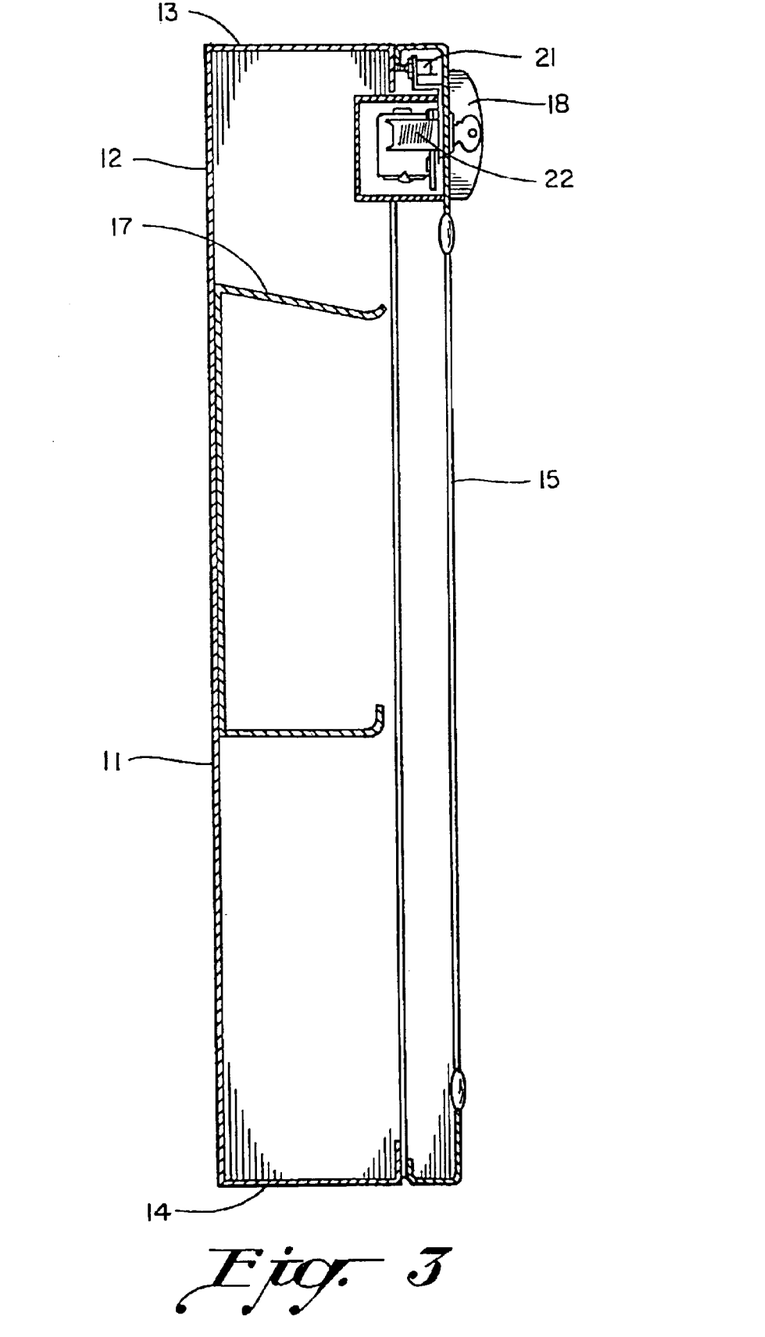
FIG. 3. A side view of the protective defibrillator storage device in FIG. 1 with the door section closed.

Referring to FIGS. 1,2 and 3, the protective defibrillator storage device 10 has an enclosure 11 comprised of a plurality of wall sections 12, a top section 13, a bottom section 14 and a door section 15. The wall sections 12, top section 13, bottom section 14 and the door section 15 define an interior compartment of sufficient size to house a defibrillator. A locking mechanism 16, 16a is typically connected to the door 15 and a wall section 12 in order to secure the door 15 in a closed position. In the preferred embodiment, the enclosure 11 is roughly 24 inches high and 14 inches wide and 3.5 inches deep. However, these dimensions may change in order to accommodate defibrillators of smaller or larger sizes.

The enclosure 11 is typically mounted onto the surface of a wall but a stabilizing base may be attached to the enclosure in order to allow the enclosure to stand on its own. In a second embodiment of the present invention, a plurality of retaining flanges 16 extend from an exterior surface of the enclosure 11. The retaining flange 16 allows the enclosure to be easily recessed into a wall, minimizing the useful space required to accommodate the protective defibrillator storage device.

The enclosure 11 is preferably made of 14 GA CRS steel with a high gloss finish, but other rigid lightweight materials can also be used. A portion of the door section 15 is preferably made of a translucent material in order to allow visibility of the interior compartment when the door section 15 is closed, a translucent synthetic plastic material is preferred.

A defibrillator mount 17 is connected to an interior surface of the enclosure. FIGS. 1, 2, and 3 show the defibrillator mount 17 attached to the back wall of the enclosure 11. However, the defibrillator mount 17 should also allow for quick removal of the defibrillator from the enclosure. The defibrillator mount 17 positions the defibrillator within the enclosure 11 so that the defibrillator may be readily viewed through the transparent portion of the door 15 by potential users of the defibrillator during a cardiac arrest situation. In the preferred embodiment, the defibrillator mount 17 is a U-shaped bracket, but there are various other types of brackets or holders which may be used to secure the defibrillator within the interior compartment and to allow greater visibility of the defibrillator while inside the enclosure 11.

Figure 8:
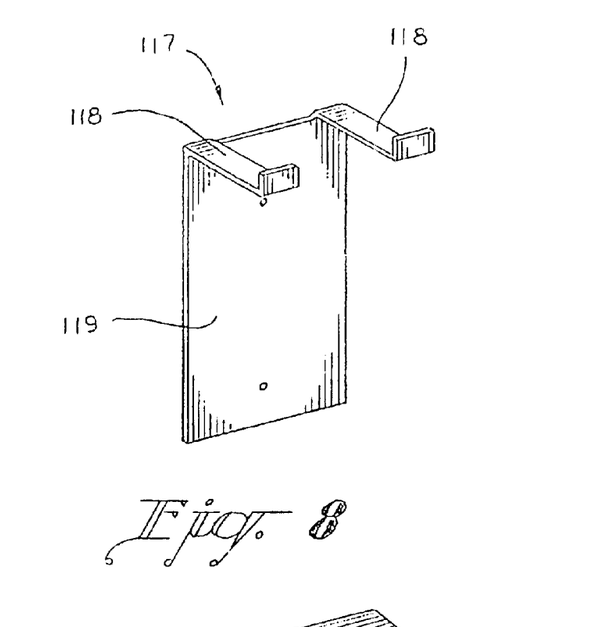
FIG. 8. A perspective view of another embodiment of the defibrillator mount.
Figure 9:
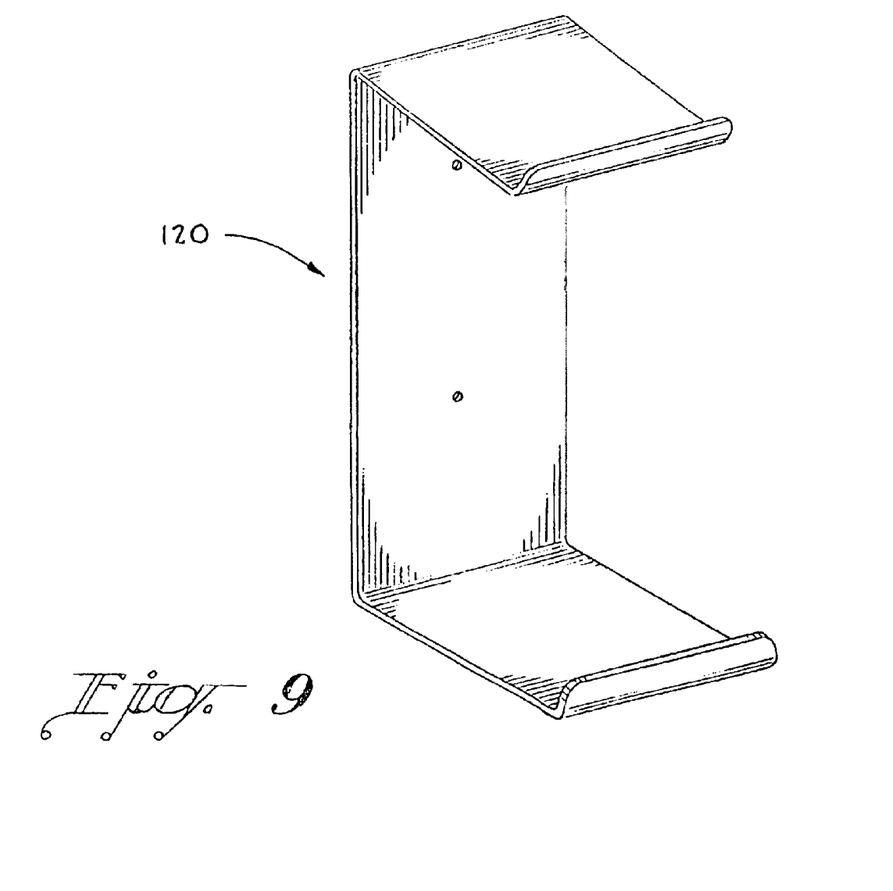
FIG. 9. A perspective view of yet another embodiment of the defibrillator mount.

FIG. 8 shows an alternate embodiment of the defibrillator mount 117 that also connects to an interior surface of the enclosure. The alternate embodiment 117 has at least one holding member 118 and a back plate 119 for connecting to the interior of the enclosure 11. FIG. 9 shows yet another embodiment of the defibrillator mount 120.

Figure 4:
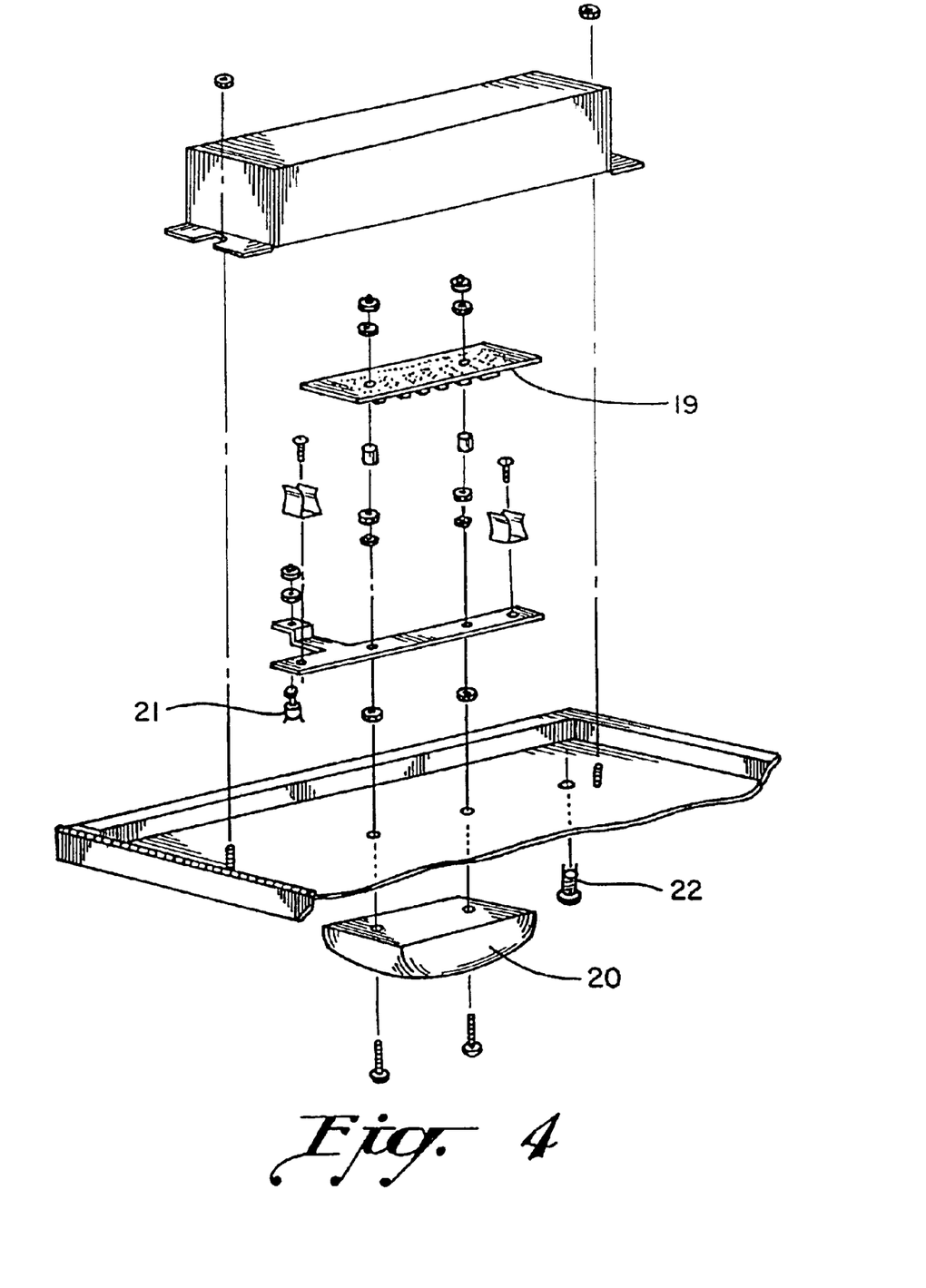
FIG. 4. An exploded view of the alarm means in FIG. 1 revealing the components of the alarm means.
Figure 5:
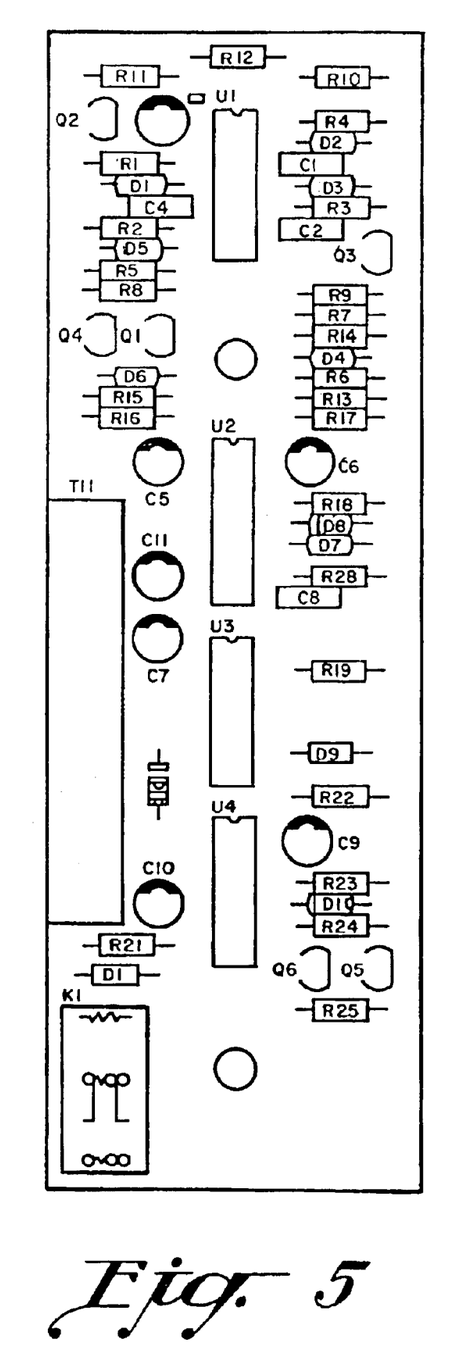
FIG. 5. An overhead planar view of the circuit board in FIG. 4.

Referring to FIGS. 3, 4, and 5, an alarm means 18 is connected to the enclosure 11. The alarm means 18 is used to indicate that the door 15 of the protective defibrillator storage device 10 has been opened, and that a cardiac arrest incident is possibly in progress. The alarm means 18 is comprised of an alarm circuit 19 with a visual alarm, preferably a strobe light, and a pair of audible alarms, preferably a siren and a buzzer connected in circuit thereto. In the preferred embodiment of the device, the strobe light and the siren are integrated into a single strobe light/siren device 20. The alarm means 18 is activated when the door section is opened.

A power source is connected in circuit to the alarm means to power the alarm circuit. In the preferred embodiment of the invention, the power source is a 9 volt battery. The power source supplies the voltage necessary to operate the alarm circuit. The alarm circuit 19 also 18 has a low battery detection means incorporated in its design. The low battery detection means detects when the battery voltage is approximately 6.2 volts and intermittently activates the audible alarm as a signal to alert that the battery voltage is low.

In the preferred embodiment, an activation switch 21 for triggering the alarm means is connected to the door section 15 and operatively positioned to contact a wall section 12 when the door section 15 is closed. In the preferred embodiment of the invention, the activation switch 21 is a pressure switch which remains open as long as there is adequate pressure on the switch. The door section 15 and a wall section 12 pressing against the switch provides the pressure to keep the switch open. Once the door section 15 is opened, the pressure on the switch is released and the switch is closed.

An alarm deactivating switch 22 is connected to the enclosure 11 and is connected in circuit to the alarm means 18. The alarm deactivating switch 22 is used to reset the system after the alarm means has been activated or to totally deactivate the alarm means 18. In the preferred embodiment, the alarm deactivating switch 22 is a key switch connecting in circuit the power supply to the alarm means. When the alarm means 18 has been activated the key switch is turned to an open position cutting off power to the alarm means and disabling the alarm. The defibrillator can then be reinserted into the protective defibrillator storage device and the door closed. The key switch is then rotated to the closed position, the circuit between the power supply and the alarm circuit is completed, and the alarm circuit is enabled.

Figure 6:
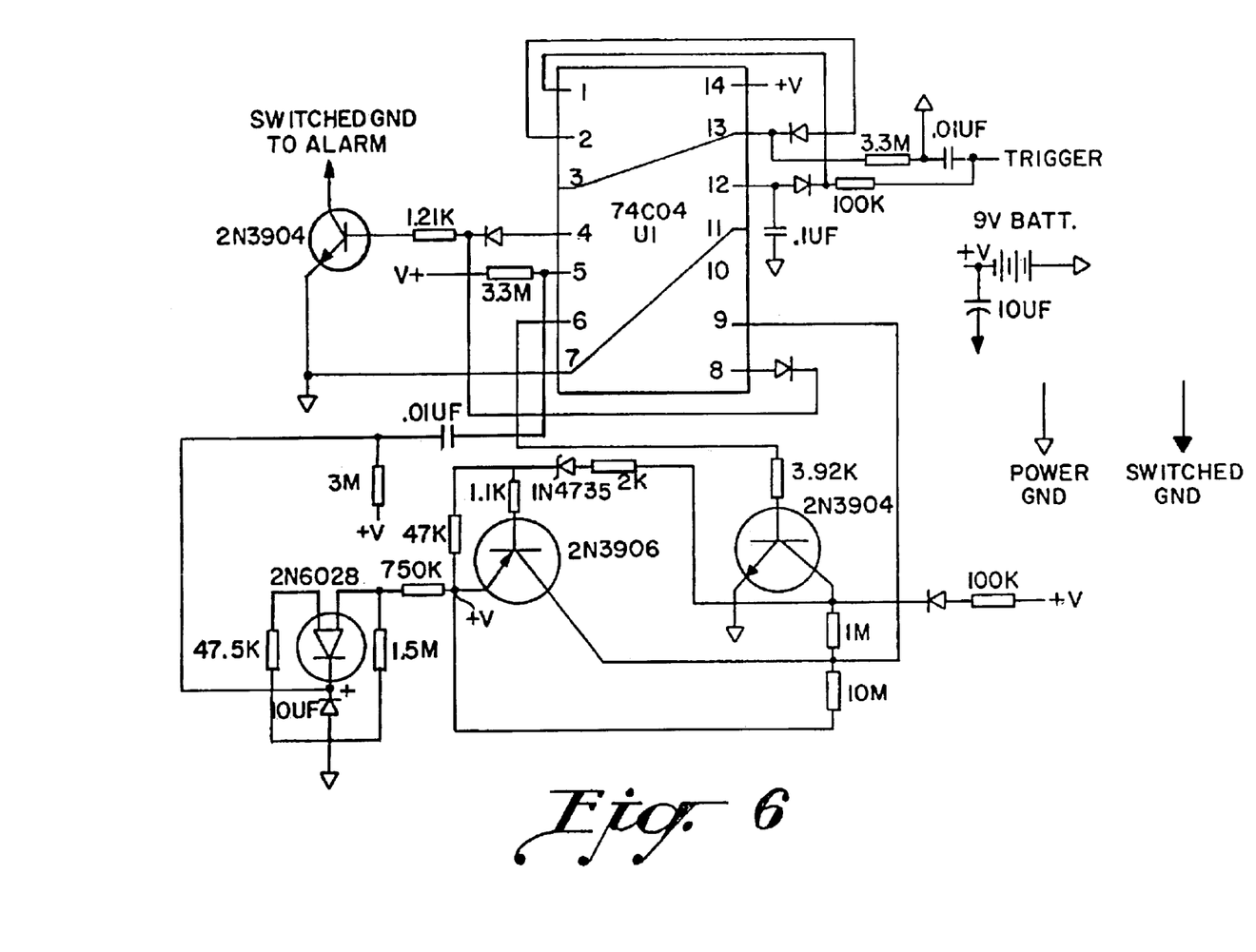
FIG. 6. A schematic view of the ground switch portion of the circuit board in FIG. 5.

Referring to FIGS. 5 and 6, in the preferred embodiment of the present invention, the power source applies nine volts to the alarm circuit 19 through the key switch. The key switch is connected in circuit to the alarm circuit 19 through a PC terminal block TB1. When the alarm deactivating switch 22 is in its closed position, a +9 volts is applied to the alarm circuit 19 through pin 3 of the PC terminal block TB1. This voltage puts hex inverter, U1 into a standby mode.

The +9 volts from the power source is also looped through the activation switch to pin 4 of the PC terminal block TB1. When the door section 15 is opened, the activation switch closes, allowing a +9 volts to be applied to pin 4 of the PC terminal block TB1 causing a triggering voltage to be applied to pin 12 of U1 causing pin 13 and 3 on U1 to go Lo and causing pin 4 on U1 to go Hi. This allows transistor Q1 to go to ground giving the alarm circuit 19 the ground necessary to activate the rest of the alarm circuit 19. The closing of the activation switch also sends a triggering voltage through pin 9 and 10 of the of the PC terminal block TB1 which can be used to trigger a remote alarm.

Figure 7:
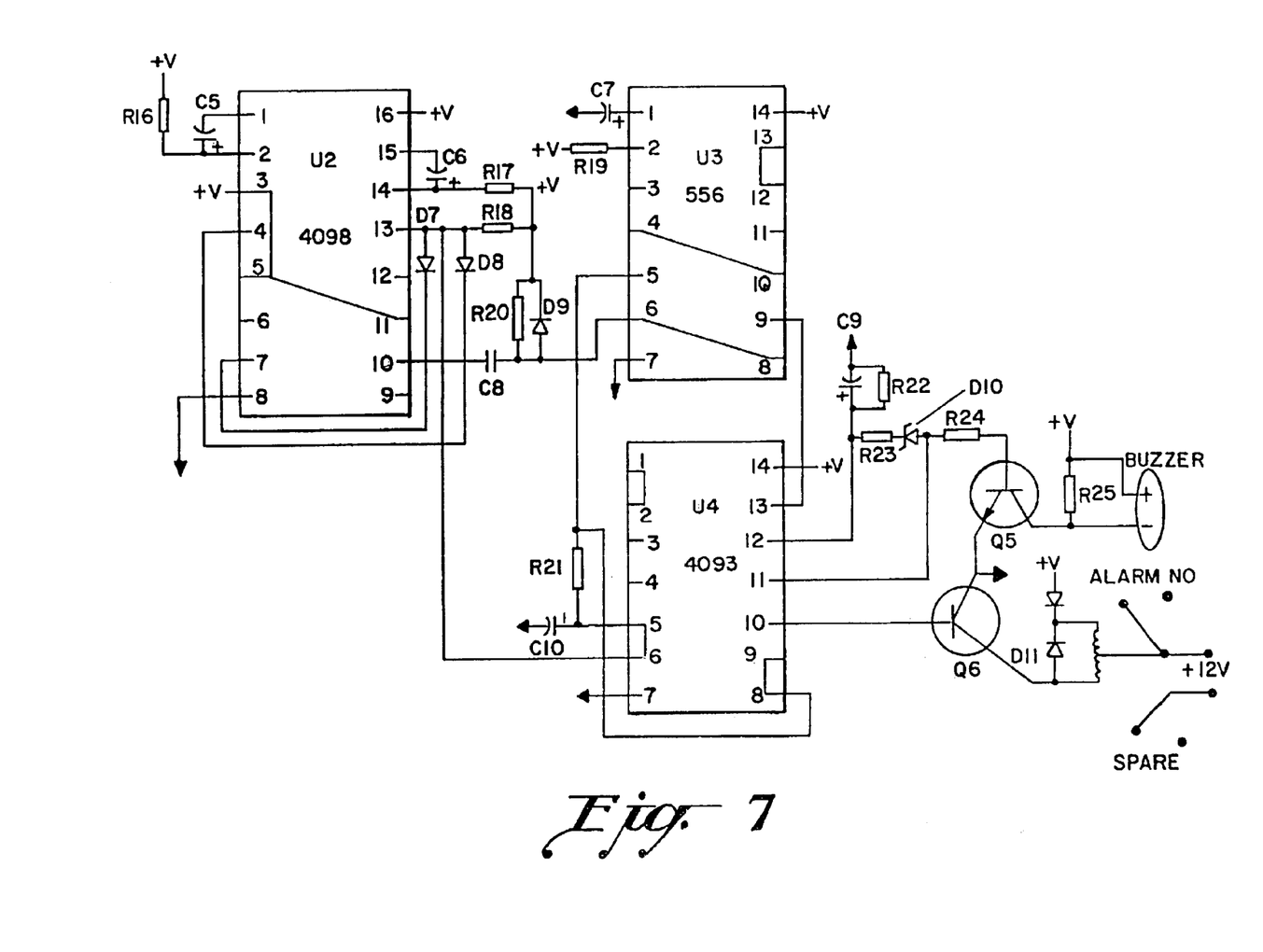
FIG. 7. A schematic view of the alarm circuit of the circuit board in FIG. 5.

Referring to FIGS. 5 and 7, in the preferred embodiment, Q1 going to ground activates integrated circuit chips U2, U3 and U4. U2 provides the necessary latching for a dual timer U3. Upon activation, pin 5 on U3 is held Hi for 30 seconds. Pin 5 causes pin 10 of U4, a Schmitt Trigger, to go Lo which causes Q6 to pull in relay coil K1 completing a circuit between a 12 volt battery and the strobe/siren device 20, activating the strobe/siren device 20. After 30 seconds, pin 5 of U3 goes Lo and pin 9 of U3 goes Hi causing pins 10 of U4 to go Hi and causing pin 12 of U4 to go Hi. The relay coil K1 is then released by Q6 and the circuit between the strobe/siren device and the 12 volt battery is broken, deactivating the strobe/siren device. The output of pin 12 on U4 is timed by C9 and R22 to cause the output of pin 11 of U4 to oscillate, driving the transistor on Q5 to activate the buzzer.

In the preferred embodiment of the present invention, a low battery detection circuit is provided by transistors Q2, Q3 and Q4. When the battery voltage drops to approximately The protective defibrillator storage 10 device is typically positioned in a highly visible and relatively accessible area. The rugged construction of the protective defibrillator storage device protects the defibrillator from inadvertent impact and provides an easily locatable housing for the defibrillator. In case of a cardiac arrest, the protective defibrillator storage device is opened triggering the alarm means 18. The audible and visual alarms alert others that a potential cardiac arrest incident may be in progress and that assistance may be needed. Since the opening of the door section triggers an audible alarm signal and a visual alarm signal, the defibrillator cabinet also acts as a deterrent to prevent tampering or theft of the defibrillator.

The invention described above is the preferred embodiment of the present invention. It is not intended that the novel device be limited thereby. The preferred embodiment may be susceptible to modifications and variations that are within the scope and fair meaning of the accompanying claims and drawings.

We claim:

1. A protective defibrillator storage device with an integral alarm system for warning others of a potential cardiac arrest incident, the protective defibrillator storage device comprising:
    an enclosure comprising a plurality of wall sections, a top section, a bottom section and a door, the wall sections, top section, bottom section and door section defining an interior compartment of sufficient size to house a defibrillator, the door partially constructed of a translucent material allowing the interior compartment to be viewed with the door closed;
    alarm means connected to the enclosure;
    an activation switch, the activation switch connected to the enclosure and connected in circuit to the alarm means, the activation switch positioned in operative relation to a wall section and the door section of the enclosure such that the opening of the door section closes the activation switch activating the alarm means; and
    a defibrillator mount connected to an interior surface of the enclosure having at least one holding member, the holding member positioning the defibrillator within the interior compartment such that the defibrillator can be readily viewed through the translucent material of the door.

2. The combination of claim 1 further comprising a key switch, the key switch connected in circuit to the alarm means, the key switch deactivating and disabling the alarm means when in an open position, and enabling the alarm means when in a closed position.

3. The protective defibrillator storage device in claim 2 further comprising a battery operated power source and a low battery detection means, the battery operated power source connected in circuit to the alarm means and the low battery detection means, the low battery detection means connected in circuit to the alarm means, the low battery detection means intermittently activating the alarm means when the battery operated power source delivers a voltage below a set voltage.

4. The protective defibrillator storage device in claim 3 wherein the alarm means is comprised of a strobe light, and a siren connected in circuit to the activation switch, the strobe light and the siren activating when the activation switch is in a closed position.

5. The protective defibrillator storage device in claim 3 wherein the alarm means is comprised of a siren, a buzzer, and a timing means, the timing means connected in circuit to the siren, buzzer and the activation switch, the timing means initially activating the siren when the activation switch switches to a closed position and then activating the buzzer and deactivating the siren after a set period of time.

6. The protective defibrillator storage device in claim 5 further comprising a relay means and a remote alarm means, the relay means connected in circuit to the activation switch and the remote alarm means, wherein the closing of the activation switch triggers the relay means to produce an electrical signal causing the remote alarm means to activate.

7. The protective defibrillator storage device in claim 6 further comprising a plurality of retaining flanges, the retaining flange extending from an exterior surface of the enclosure.

8. A protective defibrillator storage device with an integral alarm system for warning others of a potential cardiac arrest incident in combination with a defibrillator, the combination comprising:
    an enclosure comprising a plurality of wall sections, a top section, a bottom section and a door section, the wall sections, top section, bottom section and door section defining an interior compartment of sufficient size to house a defibrillator;
    alarm means connected to the enclosure;
    an activation switch, the activation switch connected to the enclosure and connected in circuit to the alarm means, the activation switch positioned in operative relation to a wall section and the door section of the enclosure such that the opening of the door section closes the activation switch activating the alarm means; and
    a defibrillator, the defibrillator placed within the interior compartment of the enclosure.

9. The combination of claim 8 further comprising a key switch, the key switch connected in circuit to the alarm means, the key switch deactivating and disabling the alarm means when in an open position, and enabling the alarm means when in a closed position.

10. The protective defibrillator storage device in claim 9 further comprising a battery operated power source and a low battery detection means, the battery operated power source connected in circuit to the alarm means and the low battery detection means, the low battery detection means connected in circuit to the alarm means, the low battery detection means intermittently activating the alarm means when the battery operated power source delivers a voltage below a set voltage.

11. The protective defibrillator storage device in claim 10 wherein the alarm means is comprised of a strobe light, and a siren connected in circuit to the activation switch, the strobe light and the siren activating when the activation switch is in a closed position.

12. The protective defibrillator storage device in claim 10 wherein the alarm means is comprised of a siren, a buzzer, and a timing means, the liming means connected in circuit to the siren, buzzer and the activation switch, the timing means initially activating the siren when the activation switch switches to a closed position and then activating the buzzer and deactivating the siren after a set period of time.

13. The protective defibrillator storage device in claim 12 further comprising a relay means and a remote alarm means, the relay means connected in circuit to the activation switch and the remote alarm means, wherein the closing of the activation switch triggers the relay means to produce an electrical signal causing the remote alarm means to activate.

14. The protective defibrillator storage device in claim 13 further comprising a plurality of retaining flanges, the retaining flange extending from an exterior surface of the enclosure.

15. A protective defibrillator storage device in combination with a defibrillator, the combination comprising:

an enclosure comprising a plurality of wall sections, a top section, a bottom section and a door section, the wall sections, top section, bottom section and door section defining an interior compartment of sufficient size to house a defibrillator the door partially constructed of a translucent material allowing the interior compartment to be viewed with the door closed;

a defibrillator mount connected to an interior surface of the enclosure having at least one holding member positioning the defibrillator within the interior compartment such that the defibrillator can be viewed through the translucent material of the door; and a defibrillator held by the defibrillator mount within the interior compartment of the enclosure.

16. The combination of claim 15 further comprising an integral alarm means connected to the enclosure.

17. The combination of claim 16 further comprising an activation switch, the activation switch connected to the enclosure and connected in circuit to the alarm means, the activation switch positioned in operative relation to a wall section and the door section of the enclosure such that the opening of the door section closes the activation switch activating the alarm means.

18. The combination of claim 17 further comprising a key switch, the key switch connected in circuit to the alarm means, the key switch deactivating and disabling the alarm means when in an open position, and enabling the alarm means when in a closed position.

19. The combination of claim 18 further comprising a battery operated power source and a low battery detection means, the battery operated power source connected in circuit to the alarm means and the low battery detection means, the low battery detection means connected in circuit to the alarm means, the low battery detection means intermittently activating the alarm means when the battery operated power source delivers a voltage below a set voltage.

20. The combination of claim 19 wherein the alarm means is comprised of a strobe light, and a siren connected in circuit to the activation switch, the strobe light and the siren activating when the activation switch is in a closed position.

21. The combination of claim 19 wherein the alarm means is comprised of a siren, a buzzer, and a timing means, the timing means connected in circuit to the siren, buzzer and the activation switch, the timing means initially activating the siren when the activation switch switches to a closed position and then activating the buzzer and deactivating the siren after a set period of time.

* * * * *

UNITED STATES PATENT AND TRADEMARK OFFICE
CERTIFICATE OF CORRECTION

PATENT NO. : 6,735,473 B2
DATED : May 11, 2004
INVENTOR(S) : Robert D. Kolder et al.

It is certified that error appears in the above-identified patent and that said Letters Patent is hereby corrected as shown below:

Column 2,
Line 43, after "does not", delete "does not", second occurrence.
Line 57, after "incident", insert -- is --.

Column 4,
Line 6, after "cutting", delete "of" and insert in place thereof -- off --.

Column 5,
Line 60, after "19", delete "also 18:".

Column 6,
Line 42, after "of the", delete "of the", second occurrence.
Line 62, delete "When the battery voltage drops to approximately".

Column 8,
Line 51, "liming" should be -- timing --.

Column 9,
Line 5, after "defibrillator", insert -- , --.

Column 10,
Line 24, insert the following claims:

-- Claim 22. A protective defibrillator storage device, the device comprising:

an enclosure comprising a plurality of wall sections, a top section, a bottom section and a door, the wall sections, top section, bottom section and door section defining an interior compartment of sufficient size to house a defibrillator, the door partially constructed of a translucent material allowing the interior compartments to be viewed with the door closed; and a defibrillator mount connected to an interior surface of the enclosure having at least one holding member, the holding member positioning the defibrillator within the interior compartment such that the defibrillator can be viewed through the translucent material of the door.

Claim 23. The device of claim 23 further comprising an integral alarm means connected to the enclosure.

UNITED STATES PATENT AND TRADEMARK OFFICE
CERTIFICATE OF CORRECTION

PATENT NO. : 6,735,473 B2
DATED : May 11, 2004
INVENTOR(S) : Robert D. Kolder et al.

It is certified that error appears in the above-identified patent and that said Letters Patent is hereby corrected as shown below:

Column 10 (cont'd),

Claim 24. The combination of claim 23 further comprising an activation switch connected to the enclosure and connected in circuit to the alarm means, the activation switch positioned in operative relation to a wall section and the door section of the enclosure such that the opening of the door section closes the activation switch activating the alarm means.

Claim 25. The device of claim 24 further comprising a key switch connected in circuit to the alarm means deactivating and disabling the alarm means when in an open position, and enabling the alarm means when in a closed position.

Claim 26. The device of claim 25 further comprising a battery operated power source connected in circuit to the alarm means and a low battery detection means connected in circuit to the alarm means, the low battery detection means intermittently activating the alarm means when the battery operated power source delivers a voltage below a set voltage.

Claim 27. The device of claim 26 wherein the alarm means is comprised of a strobe light, and a siren connected in circuit to the activation switch, the activation switch activating the strobe light and the siren when the activation switch is in a closed position.

UNITED STATES PATENT AND TRADEMARK OFFICE
CERTIFICATE OF CORRECTION

PATENT NO. : 6,735,473 B2
DATED : May 11, 2004
INVENTOR(S) : Robert D. Kolder et al.

It is certified that error appears in the above-identified patent and that said Letters Patent is hereby corrected as shown below:

<u>Column 10 (cont'd)</u>,

Claim 28. The device of claim 26 wherein the alarm means is comprised of a siren, a buzzer, and a timing means connected in circuit to the siren, buzzer and the activation switch, the timing means initially activating the siren when the activation switch switches to a closed position and then activating the buzzer and deactivating the siren after a set period of time.--

Signed and Sealed this

Twenty-second Day of March, 2005

JON W. DUDAS
*Director of the United States Patent and Trademark Office*